United States Patent [19]

Fletcher et al.

[11] 4,033,334

[45] July 5, 1977

[54] SNAP-IN COMPRESSIBLE BIOMEDICAL ELECTRODE

[76] Inventors: James C. Fletcher, Administrator of the National Aeronautics and Space Administration, with respect to an invention of; James D. Frost, Jr., Houston; Carl E. Hillman, Jr., Bellaire, both of Tex.

[22] Filed: Dec. 3, 1975

[21] Appl. No.: 637,269

[52] U.S. Cl. .............................. 128/2.1 E; 128/410; 128/DIG. 4

[51] Int. Cl.² ........................................ A61B 5/04

[58] Field of Search ........... 128/2.06 E, 2.1 R, 404, 128/410, 411, 416, 417, 418, DIG. 4, 2.1 B

[56] References Cited

UNITED STATES PATENTS

| | | | |
|---|---|---|---|
| 3,279,468 | 10/1966 | LeVine | 128/410 |
| 3,490,439 | 1/1970 | Rolston | 128/2.1 E |
| 3,508,541 | 4/1970 | Westbrook et al. | 128/2.1 B |
| 3,659,614 | 5/1972 | Jankelson | 128/410 |
| 3,669,110 | 6/1972 | Low | 128/2.1 E |
| 3,830,229 | 8/1974 | Johnson | 128/2.06 E |
| 3,976,055 | 8/1976 | Monter | 128/2.06 E |
| 3,998,213 | 12/1976 | Price | 128/2.1 B |

FOREIGN PATENTS OR APPLICATIONS

| | | | |
|---|---|---|---|
| 1,489,708 | 5/1969 | Germany | 128/410 |

OTHER PUBLICATIONS

Hanly et al., "Electrode Systems for Recording The EEG in Active Subjects", Bio Med. Electrode Technology, Academic Press, 1974, pp. 283-313.

*Primary Examiner*—Robert W. Michell
*Assistant Examiner*—Lee S. Cohen
*Attorney, Agent, or Firm*—Edward K. Fein; John R. Manning; Marvin F. Matthews

[57] ABSTRACT

A replaceable, prefilled electrode enclosed in a plastic seal and suitably adapted for attachment to a reusable, washable cap having snaps thereon is disclosed. The apparatus is particularly adapted for quick positioning of electrodes to obtain an EEG. The individual electrodes are formed of a sponge body which is filled with a conductive electrolyte gel during manufacture. The sponge body is adjacent to a base formed of a conductive plastic material. The base has at its center a male gripper snap. The cap locates the female snap to enable the electrode to be positioned. The electrode can be stored and used quickly by attaching to the female gripper snap. The snap is correctly positioned and located by mounting it in a stretchable cap. The cap is reusable with new electrodes for each use. The electrolyte gel serves as the contact electrode to achieve a good ohmic contact with the scalp.

6 Claims, 1 Drawing Figure

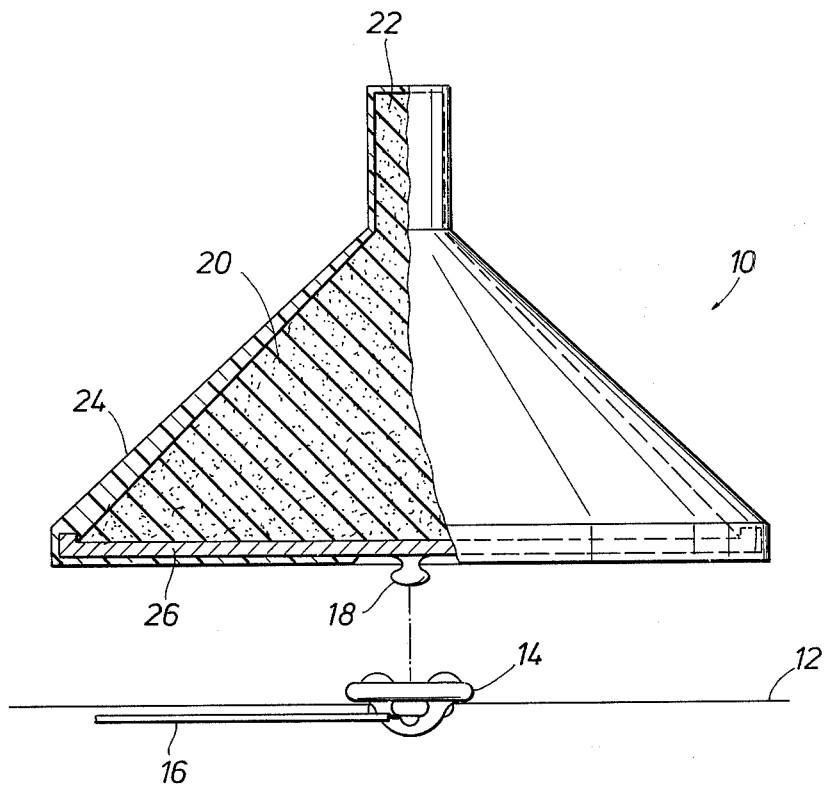

SNAP-IN COMPRESSIBLE BIOMEDICAL ELECTRODE

ORIGIN OF THE INVENTION

The invention described herein was made in the performance of work under a NASA contract and is subject to the provisions of Section 305 of the National Aeronautics and Space Act of 1958, Public Law 85–568 (72 Stat. 435; 45 U.S.C. 2457).

PRIOR ART U.S. Pat. No. 3,669,110

BACKGROUND OF THE INVENTION

The referenced patent is directed to a previously developed disposable EEG recording cap containing permanently attached compressible biomedical electrodes. It has served quite adequately. It is however somewhat expensive to use. The major expense results from the high manufacturing cost of the cap and attached electrode connector, which, while not destroyed by the recording procedure, together with the attached electrodes is disposed of after use.

With the present apparatus, it is contemplated that the electrode disclosed herein can be used with a reusable cap, thereby achieving a significant economic advantage. The fit of the cap, which is made of a stretchable material, accomplishes correct positioning of the electrodes against the scalp. The stretching of the cap at the time of the positioning of the electrodes accommodates some variations in head size. Through the use of three or four basic cap sizes, most head sizes can be accommodated. Skilled technician time is reduced. The cap incorporates a set of snaps which enable the electrodes to be positioned for reliable data collection for the EEG. The cap itself incorporates the wiring harness with the necessary conductors grouped and connected through a suitable plug or socket to enable the cap, when positioned on the user, to be connected directly to the strip chart recorder.

When the EEG has been obtained, the electrodes are quickly unsnapped and can be thrown away. The cap is stored for reuse. The sanitary purposes, it is preferably washed after each use. It can be stored and subsequently reused on the head of a person of approximately the same size. An inventory of three or four different sized caps enables practically all test subjects to be accommodated.

SUMMARY OF THE INVENTION

This invention is directed to a disposable electrode for obtaining EEG signals from a test subject. It is particularly adapted for use with a cap having a female gripper snap installed at a selected location. The female gripper snap is connected to a wire which transfers the signal to suitable recording equipment. The disposable electrode of the present invention includes a funnel shaped absorbent sponge body which has been filled with an electrolyte gel. It is preferably enclosed within a leakproof coating such as vinyl. The body has a lower flat face which is formed of a conductive plastic material. A suitable material is formed of readily moldable plastic impregnated with carbon black. The male gripper snap is located in the center of the lower face. The entire apparatus is coated with a vinyl coating to capture the gel during storage to prevent evaporation. At the time of use, the vinyl coating is punctured to enable the electrolyte gel to seep from storage in the sponge and to saturate the immediate area of contact with the scalp to obtain a good signal with controlled contact resistance.

DESCRIPTION OF THE DRAWING

The single drawing is a sectional view through the disposable electrode of the present invention disclosing details of construction and showing how it is affixed to a cap by use of male and female gripper snaps.

DESCRIPTION OF THE PREFERRED EMBODIMENT

Attention is directed to the single drawing where the numeral 10 identifies the disposable electrode of the present invention. The disposable electrode is adapted to be used with a reusable cap 12. The cap 12 is typically formed of a stretchable material such as lycra. It is sized to fit a range of heads with the stretch of the material accommodating slight variations in size and shape. The cap includes with it a plug or socket which enables all of the conductors for several electrodes to be routed through the socket for connection to a suitable amplification and recording apparatus. The cap has strategically located female gripper snaps such as the one indicated at 14. They are located so that the cap, when it has been placed on the head of the subject, positions the gripper snaps 14 at the desired locations for obtaining a suitable EEG signal. The electrodes are required to be positioned at selected locations to obtain the correct signals. If they are incorrectly positioned, the data which is obtained may not be useful.

The cap 12 thus has the gripper snap 14 installed where a portion of it is on the interior of the cap and a portion is on the exterior of the cap. The gripper snap 14 has a wire 16 welded to it and the wire 16 is adjacent to the cap and connects to a suitable plug or socket. The female gripper snap 14 has an exposed receptacle for mating with a male gripper snap 18. The two are affixed by pushing them together. They are released by pulling them apart. The gripper snap assembly is the sort typically found on children's clothing and the like.

The electrode of the present invention incorporates a sponge-like body 20. The body 20 is formed of a porous, foamed silicone rubber compound, or other suitable communicating pore sponge material. It is shaped to define a lower flat face. The body of the electrode is an inverted cone having a tab at the upper end. The tab 22 is a filling and sealing tab. The lower face of the electrode is a disc 26 of conductive plastic material. A suitable mixture is about 30% carbon in the form of particulate graphite mixed in about 70% polyethylene. The material is shaped by injection molding techniques. This percentage of carbon defines an electrode which is fairly conductive. If the concentration of carbon is increased, electrical conductivity is improved, but molding generally becomes more difficult. It has been determined that the ratio of about 30% carbon to 70% polyethylene is sufficient for most purposes.

The body of the electrode 10 is coated with a thin vinyl coating at 24. It covers the filling tab 22 and the conic surface. In addition, the vinyl coating 24 covers the lower face of the plastic disc 26. The male gripper snap 18 is embedded in the plastic disc 26. However, it is not covered over by the vinyl coating 24. The vinyl coating is relatively thin, typically in the range of three to eight mils. It can be even thinner, but this sometimes makes it a bit too fragile.

The electrode of the present invention functions in the following manner. The cap 12 is held by the user who affixes the electrode 10 by simply mating the male and female gripper snaps. The tab 22 is then cut. When it is cut, this enables the electrolyte to flow freely to moisten the area near the electrode. The electrode itself is electrically connected through the gripper snaps 14 and 18 assembled together in ohmic contact with the scalp of the user and the recording device. The cap and attached electrode are placed on the head of the subject such that the electrodes contact the scalp. Contact with the scalp is ordinarily very poor, but when the scalp is moistened with the electrolyte, the contact becomes much better. When in use, the contact with the scalp is quite good, enabling the electrode to obtain signals in the range of microvolts. At this juncture, the entire area of the scalp near the electrode is moistened in the electrolyte solution which maintains good conductivity, thereby stablizing and reducing the ohmic contact resistance to a minimum and preventing fluctuation in this value, thereby avoiding variations as a result of scalp contact.

When the device has been used, the gripper snaps are detached, and the electrode 10 is readily thrown away. Its replacement cost is minimal. The cap itself remains intact and is able to be used again. Preferably, it is washed to remove any traces of electrolyte gel from it.

The electrolyte gel is preferably injected by syringe after the vinyl coating 24 has been placed on the sponge-like body 20. The syringe is inserted through the vinyl coating. This leaves a small perforation which can be readily sealed by applying a drop of liquid vinyl or other suitable solvent to the tab. When the solvent evaporates, the hole has been resealed.

The foregoing is directed to the preferred embodiment of the electrode of the present invention, but the scope is determined by the claims which follow.

We claim:

1. A biomedical electrode assembly for use in obtaining EEG signals from a subject comprising:
    a resilient sponge-like body;
    an electrically conductive plastic base member attached to said sponge-like body, said base member having a generally planar surface;
    an electrolyte gel filling said sponge-like body;
    electrically conductive snap connector means embedded into said base member and extending outward therefrom;
    plastic coating means surrounding completely said sponge-like body and said plastic base member except for an area immediately surrounding said snap connector means extending outward therefrom, said coating means providing a leakproof barrier for said electrolyte gel;
    cap means formed of stretchable material for positioning in a predetermined pattern a plurality of said sponge-like bodies at desired locations about the head of a subject for obtaining EEG signals; and
    electrically conductive snap connector means attached to said cap means for releasably connecting both electrically and mechanically to one or more of said sponge-like bodies through corresponding snap connector means embedded into said base members thereof.

2. The apparatus of claim 1 wherein said electrically conductive plastic base member comprises a plastic material and an electrically conductive material in a ratio which will permit molding and transmittance of the desired EEG signal.

3. The apparatus of claim 2 wherein said electrically conductive material is carbon.

4. The apparatus of claim 3 wherein the ratio of said materials is about 30 percent carbon to about 70 percent plastic material.

5. The apparatus of claim 1 wherein said sponge-like body is conically shaped, and further includes filling and sealing tab means at the apex thereof for easy cutting to enable said electrolyte gel to flow from said sponge-like body.

6. The apparatus of claim 1 wherein said cap means further includes electrical conductor means attached to said snap connector means of said cap means for transferring the EEG signal to suitable recording equipment.

* * * * *